(12) United States Patent
Jach

(10) Patent No.: US 6,732,565 B1
(45) Date of Patent: May 11, 2004

(54) SENSOR ELEMENT FOR LIMIT CURRENT PROBES FOR DETERMINING THE λ VALUE OF GAS MIXTURES AND METHOD FOR ITS CALIBRATION

(75) Inventor: Olaf Jach, Boeblingen (DE)

(73) Assignee: Robert Bosch GmbH, Stuttgart (DE)

( * ) Notice: Subject to any disclaimer, the term of this patent is extended or adjusted under 35 U.S.C. 154(b) by 849 days.

(21) Appl. No.: 09/085,300

(22) Filed: May 27, 1998

(30) Foreign Application Priority Data

May 28, 1997 (DE) ......................................... 197 22 290
Mar. 28, 1998 (DE) ......................................... 198 13 919
Apr. 17, 1998 (DE) ......................................... 198 17 012

(51) Int. Cl.$^7$ ................................................ G01N 7/00
(52) U.S. Cl. ........................................ 73/1.06; 73/23.32
(58) Field of Search ............................... 73/1.06, 23.32; 204/401, 424, 425

(56) References Cited

U.S. PATENT DOCUMENTS 4,292,158 A * 9/1981 Muller et al.
4,950,380 A * 8/1990 Kurosawa et al.
5,080,765 A * 1/1992 Wang et al.
5,780,710 A * 7/1998 Murase et al. ............... 73/1.06
5,804,700 A * 9/1998 Kwon et al. .................. 73/1.06

* cited by examiner

Primary Examiner—Robert Raevis
(74) Attorney, Agent, or Firm—Kenyon & Kenyon

(57) ABSTRACT

A sensor element for limit current probes for determining the λ value of gas mixtures and a method of calibrating such sensor elements. The sensor element has an internal and an external pump electrode arranged on a ceramic body, the internal pump electrode being arranged in a diffusion channel delimited by a diffusion barrier, and a gas intake orifice running through the ceramic substrate and the diffusion channel in a direction that is essentially perpendicular to the surface of the ceramic substrate. The diffusion resistance of the diffusion barrier can be adjusted essentially linearly by selectively changing the diameter of the gas intake orifice. Calibration is performed by selecting at least one sensor element of a production lot, whose pump voltage is, measured at a selected pump current, from which the optimum diameter of the gas intake orifice can be calculated from the deviations from the ideal values using a simple ratio.

11 Claims, 1 Drawing Sheet

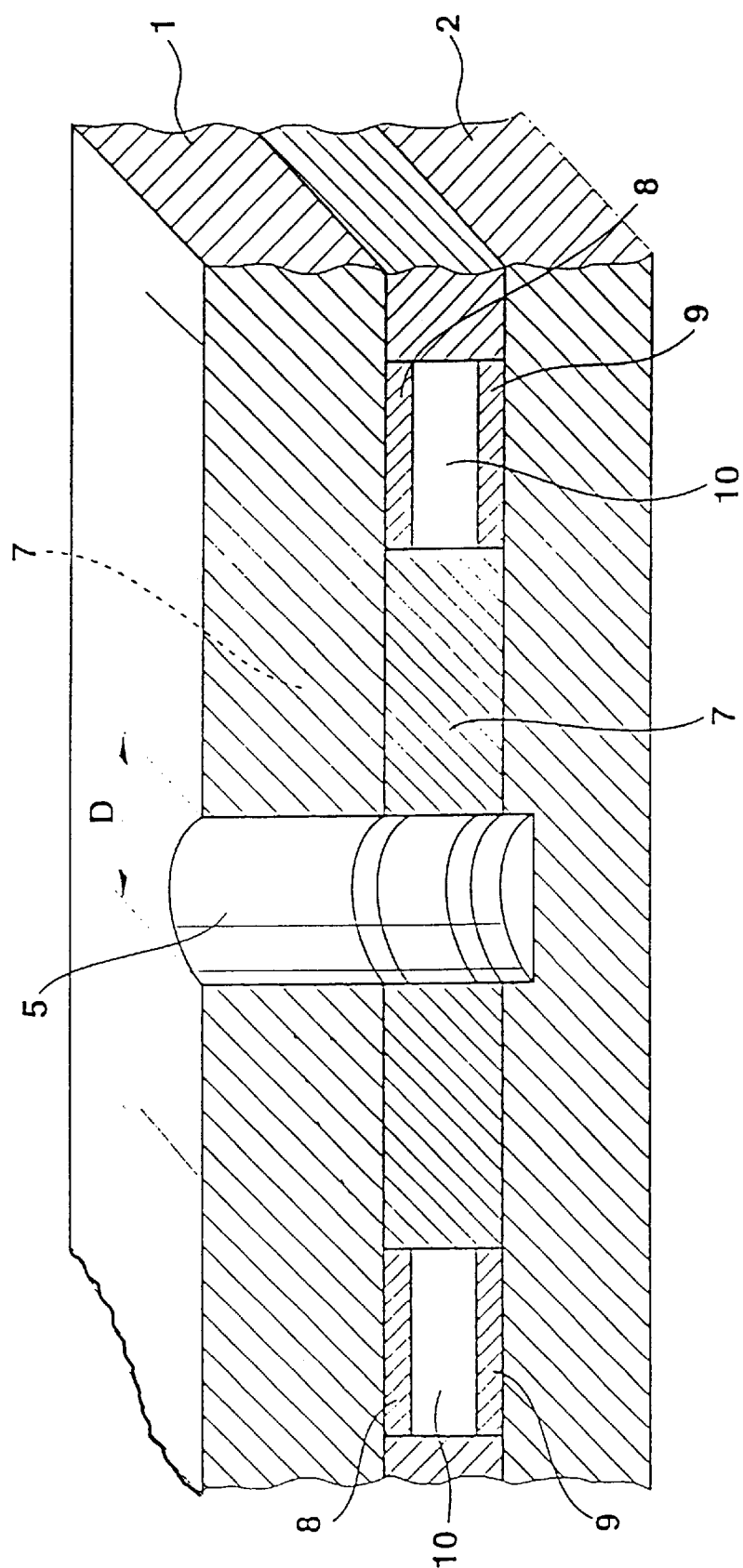

SENSOR ELEMENT FOR LIMIT CURRENT PROBES FOR DETERMINING THE λ VALUE OF GAS MIXTURES AND METHOD FOR ITS CALIBRATION

FIELD OF THE INVENTION

The present invention relates to a sensor element, in particular a sensor element for analyzing gas mixtures, for example gas mixtures in an internal combustion engine, and a method for its calibration.

BACKGROUND INFORMATION

In sensor elements operating by the diffusion limit current principle, the diffusion limit current is measured at a constant voltage applied to both electrodes of the sensor element. For an exhaust gas produced in a combustion process, this diffusion limit current depends on the oxygen concentration as long as the gas diffusion to the "pump electrode" determines the rate of the reaction taking place. Known sensors of this type operating by the polarographic measuring principle are designed so that both the anode and the cathode are exposed to the gas to be measured; the cathode has a diffusion barrier to ensure operation in the diffusion limit current range. The known limit current sensors are normally used to determine the λ value of gas mixtures, which denotes the ratio of total oxygen to the amount of oxygen needed for full combustion of the fuel, for example, of an air-fuel mixture to be burned in one cylinder; the sensor displays the oxygen level of the exhaust gas using limit current measurement with a pump voltage in a predefined range.

Thanks to simplified and inexpensive manufacturing methods, it has been proven advantageous in the past few years to industrially manufacture sensor elements made of ceramic foils using screen-printing techniques. Planar sensor elements can be more simply and inexpensively manufactured from plate- or foil-shaped oxygen-conducting solid electrolytes made, for example, of stabilized zirconium dioxide; such sensor elements are coated on both sides with an internal and an external pump electrode and with the corresponding printed circuit. The internal pump electrode is advantageously positioned in the edge area of a diffusion channel, through which the measured gas is passed, and which serves as a gas diffusion resistance.

From German Patent No. 35 43 759, European Patent No. 0 142 993, and European Patent No. 0 194 082 B1, other sensor elements and detectors are known having plate- or foil-shaped, oxygen-conducting solid electrolytes, with electrodes arranged thereon, as well as a common diffusion channel as common features.

A shortcoming with the above-described sensor elements has been that the sensor element made of plate- or foil-shaped elements contains a printed diffusion barrier, whose layer thickness is subject to natural process fluctuations because of the manufacturing technology used, in particular, final sintering of the diffusion barrier. This produces undesirable fluctuations in the pump current. To date, it has not been possible to manufacture-larger amounts of sensor elements with diffusion barriers having constant characteristics in a satisfactory and cost-effective manner, because the pump current fluctuated with each lot and had to be adjusted in a costly manner.

SUMMARY OF THE INVENTION

The advantage of the sensor element according to the invention is that the diffusion resistance of the present diffusion barrier can be linearly adjusted by selectively modifying the diameter of the gas intake orifice. The diffusion resistance can be selectively adjusted to the requirements in a simple manner by the use of a gas intake orifice produced in a subsequent operation.

Calibration during the manufacturing process of the sensor element is advantageously used for calibrating a sensor element, so that calibration can be performed in a simple manner on the blank prior to final sintering of the sensor element. Thus calibration takes place almost simultaneously with the process steps, so that the finished product does not have to be reworked in an expensive and time-consuming manner.

In a preferred embodiment, the diameter of the gas intake orifice is varied either mechanically or by laser drilling; in the latter case drilling in a particularly simple and elegant manner is made possible even after sintering.

The pump current of a sensor element for a previously defined diameter of the gas intake orifice at a previously selected pump voltage is advantageously measured. Then the measured pump current is correlated with the diameter of the intake orifice and the optimum pump current. This is possible because in a first approximation the following equation applies:

$$d_B \approx I_P,$$

where $d_B$ is the diameter of the gas intake orifice and $I_p$ is the pump current. This offers the possibility of more precisely adjusting the sensor element by varying the orifice diameter in order to set the target values of the pump current which relates to $d_B$.

Preferably, at least one sensor is selected from a lot of identical unsintered sensor elements without gas intake orifice. This allows the entire lot of hundreds or thousands of unsintered sensor elements to be calibrated prior to final sintering by using a single sensor element.

Advantageously, a gas intake orifice with a specified diameter, approximately corresponding to a pump current of 4.8 mA, is produced in this selected sensor element. Then the selected sensor element with the specified diameter of the gas intake orifice produced is sintered, so that the theoretical final characteristics of the entire lot of sensor elements can thus be characterized.

In a particularly advantageous embodiment, the pump current of this selected sintered sensor element is measured at a preselected pump voltage, preferably 1000 mV. Thus the value of the measured pump current can be adjusted to the target value and the diameter of the gas intake orifice using the above-mentioned approximation. The relationship between the measured pump current and the desired target value is obtained using a simple ratio, so that the optimum diameter of the gas intake orifice of the entire lot of sensor elements can be determined using a simple mathematical procedure.

In a preferred process step, the gas intake orifice with the optimized diameter is now produced in the lot of remaining unsintered sensor elements, so that the entire lot of unsintered sensor elements can be adjusted to the optimum pump current in this simple procedure.

BRIEF DESCRIPTION OF THE DRAWING

The FIGURE is a cross-sectional view of a portion of an exemplary sensor element according to the present invention.

DETAILED DESCRIPTION

The FIGURE schematically shows an enlarged section through one of a plurality of possible advantageous embodiments of a sensor element that can be manufactured from ceramic foils using screen printing techniques and has a pump cell operating by the limit current principle, and a concentration cell (Nernst cell). This design, however, in no way limits the present invention to this embodiment; the present invention can also be applied to pump cells that do not work together with a concentration cell. The sensor element has four solid electrolyte foils laminated together, of which only the two upper solid electrolyte foils 1,2 are illustrated. The sensor element also has a central gas intake orifice 5. An annular outer pump electrode arranged around the gas intake orifice 5 is not illustrated. In at diffusion channel 10, diffusion barrier 7 is arranged upstream from an internal pump electrode 8 and a measuring electrodes of the concentration cell. An air reference electrode, which forms together with measuring electrode 9 the concentration cell, is also not illustrated. Electrodes 9 do not extend to the gas intake orifice 5, so that a simplified adjustment can be performed using diffusion barrier 7. Electrodes 8 and 9 are arranged in an annular shape around gas intake orifice 5 and gas diffusion barrier 7.

To manufacture a sensor element according to the present invention, appropriate oxygen ion-conducting solid electrolytes, in particular on the basis of $ZrO_2$, $HfO_2$, $CeO_2$, or $ThO_2$, are used. The use of plates and foils made of yttrium-stabilized zirconium dioxide (YSZ) has proven particularly advantageous. The plates and foils advantageously have a thickness of, for example, 0.25 to 0.3 mm. The pump electrodes are advantageously made of a metal of the platinum group, in particular, of platinum, or alloys of metals of the platinum group, or alloys of metals of the platinum group with other metals. They may contain a ceramic protective material, for example, YSZ powder, in a proportion of 40% by volume, for example. They are porous and have a thickness of 8 to 15 $\mu m$, for example.

The printed circuits (not illustrated) of the pump electrodes are advantageously also made of platinum or a platinum alloy of the type described above. Pump electrodes and printed circuits can be produced by the known methods on the solid electrolyte substrate, for example, by screen printing or other known procedures. Usually there is an insulation layer made, for example, of $Al_2O_3$, between the outer pump electrode (not illustrated) and a voltage source (also not illustrated), connected by a printed conductor, and a solid electrolyte substrate. This insulation layer may have a thickness of 15 $\mu m$, for example.

The individual foils or plates forming the sensor elements are joined by processes that are customary in ceramic foil and screen printing technology, where the ceramic foils are joined and heated to approximately 100° C. Gas take orifice 5 can be prepared at this time. The orifice is advantageously produces in foil 1, for example, using a theobromine screen-printed layer; theobromine evaporates during the subsequent sintering. Thermal carbon black, which burns off during sintering, or ammonium carbonate, which evaporates, can also be used for producing diffusion channel 10. Of course, the process according to the present invention is not limited to one type of planar sensors, but can also be used for calibrating all embodiments of planar sensor elements with a gas intake orifice. The process according to the present invention is described, for convenience, with reference to a single exemplary embodiment.

A complete lot of sensor elements is manufactured up to sintering. One sensor element is then selected from the lot, a gas intake orifice 5 with a preselected diameter of approximately 0.5 mm, for example, is produced in this element, which then undergoes final sintering. After sintering this element is tested for its pump current characteristics. With this test, the orifice diameter can be calculated for the lot of remaining sensor elements. The selected sensor element has, for example, a pump current $I_d=3.65$ mA for an orifice diameter $d_B=0.4$ mm and a given pump voltage $U_p=1000$ mV. The layer thickness of the diffusion barrier is $h=0.05$ mm, for example.

Thus, for the internal surface of the gas intake orifice, the following equations apply:

$$A_{0.4} = 2 \cdot \Pi r_B \cdot h$$

$$A_{0.4} = 2 \cdot 3.14 \cdot 0.2 \text{ mm} \cdot 0.05 \text{ mm}$$

$$A_{0.4} = 0.0625 \text{ mm}^2$$

since: $A_{0.4} \approx I_{p0.4}$ the following applies: $0.0625 \text{ mm}^2 \approx 3.65$ mA An optimum pump current $I_{p(opt)}=4.8$ mA is sought. Using a ratio calculation, an optimum surface area of the gas intake orifice is determined from the above value:

$$A_{(opt)} = 0.0819 \text{ mm}^2.$$

Hence:

$$A_{(opt.)} = 2 \cdot \pi \cdot r_{opt} \cdot h$$

and therefore:

$$r_{opt} = \frac{A_{(opt.)}}{2 \cdot \pi \cdot h} = \frac{0.0819 \text{ mm}^2}{2 \cdot 3.14 \cdot 0.05 \text{ mm}} = \frac{0.0819 \text{ mm}^2}{0.314 \text{ mm}}$$

wherefrom: $r_{(opt)}=0.262$ mm. $r_{(opt)}$ is therefore the calculated optimum orifice radius, i.e., the orifice diameter $d_{(opt)}$ is 0.524 mm.

The other, unsintered sensor elements of the lot can then be corrected by the calculated radius. Because the correction is made on the blanks, it is simpler and less expensive; in addition, final sintering produces no rejects due to an incorrect diffusion limit current resulting from an incorrect gas intake orifice diameter.

What is claimed is:

1. A method of calibrating sensor elements for limit current probes, comprising the steps of:
   (a) measuring a value of a pump current of one of the sensor elements at a selected pump voltage, a gas intake orifice of the one of the sensor elements having a predetermined diameter;
   (b) correlating the measured value of the pump current with the predetermined diameter of the gas intake orifice and an optimum pump current; and
   (c) calibrating the sensor elements as a function of the correlating step, the calibrating step being performed during a manufacturing process of the sensor.

2. The method according to claim 1, further comprising the step of:
   prior to step (a), producing a lot of identical unsintered sensor elements without gas intake orifices.

3. The method according to claim 2, wherein the step of producing includes manufacturing the lot of identical unsintered sensor elements using at least one of a lamination technology and a printing technology.

4. The method according to claim 2, further comprising the steps of:
   prior to step (a), selecting the one of the sensor elements from the lot of the identical unsintered sensor elements, and producing the gas intake orifice in the one of the sensor elements.

5. The method according to claim 4, further comprising the step of the step of:

prior to step (a), sintering the one of the sensor elements.

6. The method according to claim 5, wherein step (b) includes the step of:

adjusting the value of the pump current using the optimum pump current and the diameter of the gas intake orifice.

7. The method according to claim 6, wherein step (b) further includes the step of:

determining an optimized diameter of the gas intake orifice as a function of the adjusted value of the pump current.

8. The method according to claim 7, further comprising the step of:

producing a gas intake orifice having the optimized diameter in each of the unsintered sensor elements.

9. The method according to claim 8, further comprising the step of:

sintering each of the unsintered sensor elements provided with the gas intake orifice having the optimized diameter.

10. A method for calibrating sensor elements for limit current probes, comprising the steps of:

selecting a first sensor element from the sensor elements;

introducing a first gas intake orifice into the first sensor element, the first gas intake orifice having a predetermined diameter;

applying a preselected pump voltage to the selected sensor element;

measuring a pump current of the selected sensor;

determining an optimal diameter of a second gas intake orifice for a second sensor element as a function of a value of the measured pump current, the predetermined diameter of the first gas intake orifice, and a preselected optimum pump current; and introducing the second gas intake orifice having the optimal diameter the second sensor element.

11. A method for calibrating a sensor element for a limit current probes, comprising the steps of:

modifying a diameter of a gas intake orifice of the sensor element in a controlled manner; and adjusting a diffusion resistance of a diffusion barrier of the sensor element to a preselected pump current as a function of the modifying step.

* * * * *